United States Patent [19]

Gilbert et al.

[11] Patent Number: 5,786,520

[45] Date of Patent: Jul. 28, 1998

[54] O-ALKYLATION OF PHENOLIC COMPOUNDS VIA RARE EARTH ORTHOPHOSPHATE CATALYSTS

[75] Inventors: Laurent Gilbert; Marcelle Janin, both of Lyons; Anne-Marie Le Govic, Paris; Philippe-Jean Tirel, Oullins, all of France

[73] Assignee: Rhone-Poulenc Chimie, Courbevoie Cedex, France

[21] Appl. No.: 732,831

[22] Filed: Oct. 15, 1996

Related U.S. Application Data

[63] Continuation of Ser. No. 420,709, Apr. 11, 1995, abandoned, which is a continuation of Ser. No. 157,284, Nov. 26, 1993, abandoned.

[30] Foreign Application Priority Data

Nov. 25, 1992 [FR] France ................... 92 14154

[51] Int. Cl.$^6$ ................................................. C07C 43/02
[52] U.S. Cl. .................. 568/630; 568/632; 568/635; 568/657
[58] Field of Search .......................... 568/630, 632, 568/635, 657

[56] References Cited

U.S. PATENT DOCUMENTS 4,450,306  5/1984  Eskinazi et al. .
4,533,758  8/1985  Wells et al. .
4,675,456  6/1987  Mossman et al. .

FOREIGN PATENT DOCUMENTS 0420756  4/1991  European Pat. Off. .

Primary Examiner—Joseph K. McKane
Attorney, Agent, or Firm—Burns, Doane, Swecker & Mathis, L.L.P.

[57] ABSTRACT

Carbocyclic/aliphatic ethers, for example anisole, quaicol, guaethol, p-methoxyphenol and ethylene dioxybenzene, are selectively prepared, in good yield, by reacting a phenolic compound, for example a phenol, hydroquinone, pyrocatechin, naphthol, or the like, with an alcohol, for example methanol, ethanol, isopropanol, ethylene glycol, etc., in gaseous phase, in the presence of a catalytically effective amount of a trivalent rare earth metal orthophosphate, for example a lanthanum, cerium or samarium orthophosphate, optionally doped with an alkali or alkaline earth metal, preferably cesium.

33 Claims, No Drawings

5,786,520

O-ALKYLATION OF PHENOLIC COMPOUNDS VIA RARE EARTH ORTHOPHOSPHATE CATALYSTS

This application is a continuation, of application Ser. No. 08/420,709, filed Apr. 11, 1995, now abandoned, in turn a continuation of application Ser. No. 08/157,284, filed on Nov. 26, 1993, and now abandoned.

BACKGROUND OF THE INVENTION

1. Field of the Invention

The present invention relates to the O-alkylation of phenolic compounds for the preparation of carbocyclic/aliphatic ethers via rare earth metal orthophosphate catalysis, and, more especially, to the preparation of such ethers from diphenolic compounds.

2. Description of the Prior Art

A wide variety of processes are known to this art for preparing ethers from phenolic compounds.

One conventional process comprises reacting phenol with an alcohol in liquid phase, or in gaseous phase, in the presence of a catalyst.

Thus, FR-A-2,149,461 describes a process for the preparation of monomethyl ethers of diphenols in liquid phase, comprising reacting the diphenol to be etherified, at a high temperature ranging from 200° C. to 240° C., with methanol, in the presence of a boron phosphate catalyst. This process must be carried out under high pressure; hence, special apparatus is required.

The literature, patent and otherwise, also describes various processes for the preparation of ethers of diphenols in gaseous phase.

DE-A-827,803 describes a process for preparing a monomethyl ether from pyrocatechin, by reacting pyrocatechin with methanol, in gaseous phase at a temperature ranging from 250° C. to 300° C., in the presence of boron phosphate or silica gel vermicelli impregnated with phosphoric acid. The degree of conversion of the pyrocatechin is 64.9%, and the degree of selectivity of the guaiacol is 54.6% and 11.5% relative to the veratrole.

When boron phosphate is used as the catalyst, the catalytic activity of the catalyst is good, since the degree of conversion of the pyrocatechin ranges from 50% to 65% and the selectivity of the guaiacol is also good, i.e., about 80% to 90%. However, when the catalyst is used in a continuous process, it no longer is satisfactory because the boron phosphate reacts with the pyrocatechin and is eluted thereby. Catalytic loss then occurs, as does a reduction in catalytic activity, when the operation is lengthy.

To overcome this drawback, use of a catalyst containing aluminum, boron and phosphorus has been described (FR-A-2,303,784). Such a catalyst permits good conversion of the diphenol, but despite the fact that it has a longer life, this remains to be improved because boron phosphate is also consumed.

EP-A-0,420,756 describes using a catalyst, the active phase of which comprising a phosphorus compound such as phosphoric acid and/or a product from the reaction of a phosphorus compound and a boron compound, such as boron phosphate, said active phase being deposited onto suitable support. In order to compensate for catalytic loss, continuous introduction of the active phase is described, with feed gases which permits the support to be impregnated by the active phase. This presents a problem in respect of purifying the final product, which contains methyl borate and phosphoric acid.

SUMMARY OF THE INVENTION

Accordingly, a major object of the present invention is the provision of an improved process for the O-alkylation of mono- or polyhydroxylated phenols which avoids or conspicuously ameliorates the above disadvantages and drawbacks to date characterizing the state of this art, notably the aforesaid loss of catalytic activity.

Another object of the present invention is the provision of a catalyst permitting the preparation of O-alkylated diphenols, while modulating production of the final phenolic ethers. Stated differently, an improved process is hereby provided which, depending upon the particular catalyst selected, permits the selective preparation of a diphenol monoalkyl ether, or a mixture of a diphenol monoalkyl ether and a diphenol dialkyl ether (e.g., depending upon market requirements).

Briefly, the present invention features the O-alkylation of a phenolic compound, comprising reacting said phenolic compound with an alkanol, in gaseous phase, in the presence of a catalytically effective amount of a catalyst selected from among the trivalent rare earth metal orthophosphates.

DETAILED DESCRIPTION OF PREFERRED EMBODIMENTS OF THE INVENTION

More particularly according to the present invention, by the term "phenolic compound" is intended an aromatic compound or nucleus bearing at least one hydroxyl group substituent. The term "aromatic compound" connotes the conventional definition of aromaticity, as set forth, in particular by Jerry March, *Advanced Organic Chemistry*, pp. 37 et seq., 3rd edition, John Wiley and Sons (1985).

By the term "rare earth metals" are intended the lanthanides having an atomic number of from 57 to 71, as well as yttrium and also scandium.

By the term "trivalent rare earth metal orthophosphates" are intended compounds in which the molar ratio between the phosphate anion and the trivalent rare earth cation is about 1±0.2, preferably 1.0.

In one preferred embodiment of the process of the invention, a rare earth orthophosphate is used which is calcined at a high temperature.

In another preferred embodiment of the invention, a trivalent rare earth orthophosphate is used which is impregnated, or doped, with an alkali metal or an alkaline earth metal.

Too, by the term "doping agent" or "dopant" are intended such alkali metal or alkaline earth metal values.

According to the process of the invention, a phenolic compound is reacted with an alkanol, in gaseous phase, in the presence of a catalytically effective amount of a catalyst selected from among rare earth metal phosphates which either may or may not be doped.

In particular, the present invention features a process for the O-alkylation of a phenolic compound having the general formula (I):

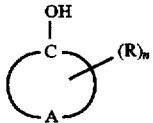

wherein A is the residue of a monocyclic or polycyclic, aromatic carbocyclic radical, or a divalent radical comprising a structural unit or chain of two or more monocyclic aromatic carbocyclic radicals, R is one or more "inert" substituents, which may be the same or different, and n is a number less than or equal to 5, with an alcohol having the general formula (II):

 (II)

wherein R' is a hydrocarbon radical having from 1 to 24 carbon atoms, notably a linear or branched, saturated or unsaturated acyclic aliphatic radical; a monocyclic or polycyclic, saturated or unsaturated cycloaliphatic radical; or a linear or branched, saturated or unsaturated aliphatic radical bearing a cyclic substituent.

The term "alkanol" will ofttimes be used hereinafter to generically designate all of the alcohols which correspond to formula (II).

According to the process of the invention, the phenolic compound of formula (I) is reacted with the alkanol in gaseous phase. This comprehends that the various reagents are vaporized under the conditions of reaction, but does not exclude the presence of a possible liquid phase resulting either from the physical properties of the reagents, or from conducting the reaction under pressure, or using an organic solvent.

The process of the invention is carried out using any phenolic compound corresponding to general formula (I), and, more particularly, using phenolic compounds of formula (I), wherein the radicals R, which may be the same or different, are each a hydrogen atom; a linear or branched alkyl radical having from 1 to 6 carbon atoms, preferably having from 1 to 4 carbon atoms, such as methyl, ethyl, propyl, isopropyl, butyl, isobutyl, sec-butyl and tert-butyl radicals; a linear or branched alkenyl radical having from 2 to 6 carbon atoms, preferably having from 2 to 4 carbon atoms, such as vinyl and allyl radicals; a linear or branched alkoxy radical having from 1 to 6 carbon atoms, preferably having from 1 to 4 carbon atoms, such as the methoxy, ethoxy, propoxy, isopropoxy and butoxy radicals; an acyl radical having from 2 to 6 carbon atoms; or a radical of the formulae:

—$R_1$—OH
—$R_1$—$COOR_2$
—$R_1$—CHO
—$R_1$—$NO_2$
—$R_1$—CN
—$R_1$—$(NR_2)_2$
—$R_1$—CO—$(NR_2)_2$
—$R_1$—X
—$R_1$—$CF_3$ in which formulae, $R_1$ is a simple valence bond or a saturated or unsaturated, linear or branched, divalent hydrocarbon radical having from 1 to 6 carbon atoms, such as methylene, ethylene, propylene, isopropylene and isopropylidene radicals; $R_2$ is a hydrogen atom or a linear or branched alkyl radical having from 1 to 6 carbon atoms; and X is a halogen atom, preferably a chlorine, bromine or fluorine atom.

The phenolic compound of formula (I) can be substituted by one or more substituents, examples of which are given below. Any substituent can be present on the cyclic nucleus provided that it does not interfere with the reaction/desired final product, i.e., is "inert." If the substituent bears a hydrogen atom, same can be replaced by the radical R' borne by the alkanol and, if it bears an alkyl radical $R_2$, this will be exchanged for R' if R' and $R_2$ are different alkyl radicals.

Particularly exemplary phenolic compounds corresponding to formula (I) are those in which R is:

(i) a hydrogen atom,
(ii) an OH group,
(iii) a linear or branched alkyl radical having from 1 to 6 carbon atoms,
(iv) a linear or branched alkenyl radical having from 2 to 6 carbon atoms,
(v) a linear or branched alkoxy radical having from 1 to 6 carbon atoms,
(vi) a —CHO group,
(vii) an acyl radical having from 2 to 6 carbon atoms,
(viii) a —$COOR_2$ group wherein $R_2$ is as defined above,
(ix) a —$NO_2$ group,
(x) a halogen atom, preferably a fluorine, chlorine or bromine atom,
(xi) a —$CF_3$ group; and n is a number equal to 0, 1, 2 or 3.

Other particularly preferred compounds of formula (I) are those wherein the residue (A) represents:

(1) a monocyclic or polycyclic aromatic carbocyclic radical, the cyclic moieties of which together form an orthocondensed structural unit corresponding to formula (Ia):

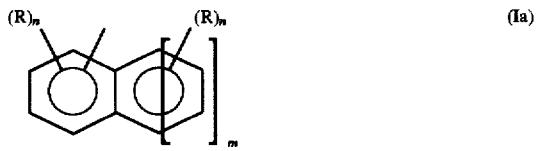 (Ia)

in which m is a number equal to 0, 1 or 2 and R and n, which may be the same or different, are as defined above; or (2) a radical comprising a backbone or structural unit of two or more monocyclic aromatic carbocyclic radicals corresponding to the formula (Ib):

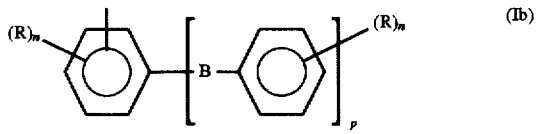 (Ib)

in which R and n, which may be identical or different, are as defined above, p is a number equal to 0, 1, 2 or 3 and B is a simple valence bond, an alkylene or alkylidene radical having from 1 to 4 carbon atoms, preferably a methylene or isopropylidene radical, or one of the radicals of the formulae:

—O—, —CO—, —COO—, —OCOO—,
—S—, —SO—, —$SO_2$—,

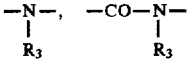

wherein $R_3$ is a hydrogen atom, an alkyl radical having from 1 to 4 carbon atoms, or a cyclohexyl or phenyl radical.

The preferred compounds of formula (I) corresponding to formulae (Ia) and (Ib) are those in which R is a hydrogen atom, a hydroxyl group, a —CHO group, an —$NO_2$ group, a linear or branched alkyl or alkoxy radical having from 1 to 6 carbon atoms, preferably 1 to 4 carbon atoms; B is a simple valence bond, an alkylidene or alkylene radical having from 1 to 4 carbon atoms, or an oxygen atom; m is equal to 0 or 1; n is equal to 0, 1 or 2; and p is equal to 0 or 1.

Even more preferred compounds of formula (I) are those in which R is a hydrogen atom, a hydroxyl group, a methyl radical, or a methoxy radical.

Particularly exemplary compounds of formula (I) include those wherein the residue A corresponds to formula (1a) in which m and n are equal to 0, such as phenol; those wherein the residue A corresponds to formula (1a) in which m is equal to 0 and n is equal to 1, such as:

Hydroquinone,
Pyrocatechin,
Resorcinol,
o-Cresol,
m-Cresol,
p-Cresol,
2-Ethylphenol,
3-Ethylphenol,
4-Ethylphenol,
2-Propylphenol,
4-Propylphenol,
2-Sec-butyl phenol,
2-Tert-butyl phenol,
3-Tert-butyl phenol,
4-Tert-butyl phenol,
4-Sec-butyl phenol,
2-Methoxyphenol,
3-Methoxyphenol,
4-Methoxyphenol,
2-Ethoxyphenol,
3-Ethoxyphenol,
4-Ethoxyphenol,
Salicylic aldehyde,
p-Hydroxybenzaldehyde,
Methyl salicylate,
Methyl ester of p-hydroxybenzoic acid,
2-Chlorophenol,
3-Chlorophenol,
4-Chlorophenol,
2-Nitrophenol,
3-Nitrophenol,
4-Nitrophenol,
N-Acetyl-para-aminophenol;

those in which the residue A corresponds to formula (1a) in which m is equal to 0 and n is equal to 2, such as:

2,3-Dimethylphenol,
2,4-Dimethylphenol,
2,5-Dimethylphenol,
2,6-Dimethylphenol,
3,4-Dimethylphenol,
3,5-Dimethylphenol,
Vanillin,
Isovanillin,
2-Hydroxy-5-acetamidobenzaldehyde,
2-Hydroxy-5-propionamidobenzaldehyde,
4-Allyloxybenzaldehyde,
2,3-Dichlorophenol,
2,4-Dichlorophenol,
2,5-Dichlorophenol,
2,6-Dichlorophenol,
3,4-Dichlorophenol,
3,5-Dichlorophenol,
Methylhydroquinone,
Chlorohydroquinone,
Pyrogallol; those in which the residue A corresponds to formula (1a) in which m is equal to 0 and n is equal to 3, such as:

4-Bromovanillin,
4-Hydroxyvanillin,
2,3,5-Trimethylphenol,
2,3,6-Trimethylphenol,
2,4,6-Trimethylphenol,
3,4,5-Trimethylphenol,
2,4,6-Tri-tert-butylphenol,
2,4-Di-tert-butylphenol,
2,6-Di-tert-butylphenol,
3,5-Di-tert-butylphenol,
2,6-Di-tert-butyl-4-methylphenol,
2,6-Dimethyl-4-tert-butylphenol,
2,4,6-Trinitrophenol,
2,4,6-Trichlorophenol,
2,3,4-Trichlorophenol,
2,3,5-Trichlorophenol,
2,3,6-Trichlorophenol,
Dichlorohydroquinones,
3,5-Dimethoxy-4-hydroxybenzaldehyde; those in which the residue A corresponds to formula (1a) in which m is equal to 1 and n is greater than or equal to 1, such as:

1,2-Dihydroxynaphthalene,
1,4-Dihydroxynaphthalene,
1,5-Dihydroxynaphthalene,
2,3-Dihydroxynaphthalene,
2,6-Dihydroxynaphthalene,
2,7-Dihydroxynaphthalene,
4-Methoxy-1-naphthol,
6-Bromo-2-naphthol; and those in which the residue A corresponds to formula (1b) in which n is greater than or equal to 1, such as:

2-Phenoxyphenol,
3-Phenoxyphenol,
Phenylhydroquinone,
4,4'-Dihydroxybiphenyl,
4,4'-Isopropylidenediphenol (bisphenol A),
Bis(4-hydroxyphenyl)methane,
Bis(4-hydroxyphenyl)sulfone,
Bis(4-hydroxyphenyl)sulfoxide,
Tetrabromobisphenol A.

The alkanol employed in the process of the invention advantageously corresponds to formula (II) in which R' is a linear or branched, saturated or unsaturated, acyclic aliphatic radical.

In particular, R' is a linear or branched, alkynyl, alkadienyl, alkenyl, or alkyl radical, preferably having from 1 to 24 carbon atoms.

The hydrocarbon chain or backbone of the radicals R' is optionally interrupted by one of the following groups: —O—, —CO—,—COO, OCOO—, —S—, —SO$_2$—,

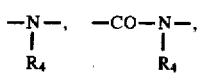

in which $R_4$ is a hydrogen atom, or a linear or branched alkyl radical having from 1 to 4 carbon atoms, preferably a methyl or ethyl radical, and/or is substituted by one of the following substituents:

—OH, —OCOO—, —COOR$_4$, —CHO, —NO$_2$, —X—, —CF$_3$ wherein $R_4$ is as defined above.

The linear or branched, saturated or unsaturated acyclic aliphatic residue is optionally substituted by a cyclic substituent. By "cyclic" is intended an aromatic, saturated or unsaturated, heterocyclic or carbocyclic ring member.

The acyclic aliphatic residue can be bonded to the cyclic moiety via a valence bond or by one of the following groups:

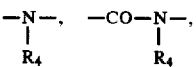

wherein $R_4$ is as defined above.

Exemplary such cyclic substituents are heterocyclic, aromatic or cycloaliphatic substituents, in particular cycloaliphatic substituents having 6 carbon atoms in the ring, or benzene substituents, these cyclic substituents themselves optionally being substituted by 1, 2, 3, 4 or 5 of the radicals $R_5$ which may be the same or different, with $R_5$ being as defined above in resect of the radical R borne by the compounds of formula (I). The preferred cyclic substituents are benzene nuclei.

In the alkanols of formula (II), R' can also be a saturated carbocyclic radical, or one containing either 1 or 2 ethylenic double bonds in the ring member, usually having from 3 to 7 carbon atoms, preferably having 6 carbon atoms in the ring. Such cyclic radicals can be substituted by 1 to 5 $R_5$ radicals, preferably 1 to 3, with the $R_5$ radicals being as defined above.

Preferred examples of R' radicals are cyclohexyl or cyclohexenyl radicals, optionally substituted by linear or branched alkyl radicals having from 1 to 4 carbon atoms.

The process of the invention is easily carried out using most alkanols. Exemplary such alkanols include the lower aliphatic alkanols having 1 to 5 carbon atoms, such as methanol, ethanol, trifluoroethanol, propanol, isopropyl alcohol, butanol, isobutyl alcohol, sec-butyl alcohol, tert-butyl alcohol, pentanol, isopentyl alcohol, sec-pentyl alcohol and tert-pentyl alcohol, monoethyl ether of ethylene glycol, methyl lactate, isobutyl lactate, methyl D-lactate, isobutyl D-lactate, and also higher aliphatic alcohols having at least 6 and up to about 20 carbon atoms, such as hexanol, heptanol, isoheptyl alcohol, octanol, isooctyl alcohol, 2-ethylhexanol, sec-octyl alcohol, tert-octyl alcohol, nonanol, isononyl alcohol, decanol, dodecanol, tetradecanol, octadecanol, hexadecanol, oleyl alcohol, eicosyl alcohol, monoethyl ether of diethylene glycol. Cycloaliphatic alcohols having 3 to about 20 carbon atoms are also exemplary, such as cyclopropanol, cyclobutanol, cyclopentanol, cyclohexanol, cycloheptanol, cyclooctanol, cyclododecanol, tripropylcyclohexanol, methylcyclohexanol and methylcycloheptanol, as are aliphatic alcohols substituted by aromatic radicals having 7 to about 20 carbon atoms, such as benzyl alcohol, phenethyl alcohol, phenylpropyl alcohol, phenyloctadecyl alcohol and naphthyldecyl alcohol.

It is also possible to use polyols, in particular polyoxyethylene glycols such as ethylene glycol, diethylene glycol, triethylene glycol, propylene glycol, glycerol, etc.

Among the aforesaid alcohols, it is preferred to employ primary or secondary alcohols having from 1 to 4 carbon atoms in the process of the invention.

The preferred alcohols are methanol, ethanol, isopropanol and ethylene glycol.

With particular respect to the catalyst of the invention, advantageously it has the following formula:

$$MPO_4(1m)_p \qquad (III)$$

wherein M is an $M_3$ trivalent rare earth, or a mixture of at least one $M_3$ trivalent rare earth and at least one element selected from among the $M_1$ alkali metals and the $M_2$ alkaline earth metals according to the equation:

1 m is a basic impregnation compound comprising an alkali metal or alkaline earth metal, preferably an alkali metal, and mixtures thereof, associated with a counter-anion to provide electrical neutrality; α is a coefficient ranging from 0 to 3, advantageously greater than 0.01 and at most equal to 0.5, preferably 0.05 to 0.2; β is a coefficient ranging from 0 to ½, preferably ranging from 0 to ⅓ or 1±0.1; γ is a coefficient ranging from 0 to 1, advantageously at least equal to ⅓, preferably equal to ½; and p is a number less than 0.5 and advantageously ranges from 0.04 to 0.25.

For a classification of such elements, reference is made hereinafter to the Periodic Table of elements published in the Bulletin of the Société Chimique de France, No. 1 (1966).

In formula (III), the various elements are as follows:

$M_1$ is selected from among the elements in Column 1A and mixtures thereof, preferably alkali metals such as lithium, sodium, potassium, rubidium and cesium, $M_2$ is selected from among the elements in column 2A and mixtures thereof, preferably alkaline earth metals such as beryllium, magnesium, calcium, strontium and barium, and $M_3$ is selected from among the trivalent rare earths, including the lanthanides, yttrium, scandium and mixtures thereof, preferably the lanthanides such as lanthanum, cerium, praseodymium, neodymium, samarium, europium, gadolinium, terbium, dysprosium, holmium, erbium, thulium, ytterbium and lutecium.

Usually, M is constituted by a maximum of three elements, for convenience; for the same reason, it can be economically desirable to use commercial mixtures of rare earths in whatever form, provided that they readily form the compounds according to the invention. Thus, although not critical, γ very often varies slightly from unity (0.9±0.1) and M is only one metal short of impurities.

1 m is an impregnation compound comprising an alkali or alkaline earth metal, preferably an alkali metal, and mixtures thereof, associated with one or more counter-anions to provided electrical neutrality.

The initial counter-anion(s), namely, those existing prior to a heat treatment, are preferably selected from among such anions as nitrate, sulfate, chloride, fluoride, hydrogenophosphate, phosphate, hydrogenosulfate, oxalate, acetate, benzoate, and the like.

The anions can be of one single species or a mixture of species; for the sake of simplicity, it is preferable to use only one single species or only one single species family.

The content of doping agent in the catalyst is typically such that the percentage by weight of doping agent, expressed as alkali metal and/or alkaline earth metal relative to the phosphate of the dry trivalent rare earth, ranges from 0% to 25%, preferably from 3% to 15% by weight.

In one embodiment of the process of the invention, an orthophosphate of a trivalent rare earth is used which is not doped. The catalyst then corresponds to formula (III) in which $\alpha$ and $\beta$ are equal to 0. In this event, as more fully explained below, one preferred embodiment entails the use of a catalyst which has first been subjected to calcination at a high temperature.

Exemplary catalysts suitable for the process of the invention include a first family containing orthophosphates of the light rare earths, designated the ceric rare earths, including the elements La, Ce, Pr, Nd, Sm, Eu. Said orthophosphates are dimorphic, they have a hexagonal structure and evolve into a monoclinic structure when they are heated at a temperature of 600° to 800° C.

A second family of orthophosphates of rare earths according to the invention includes Gd, Tb and Dy orthophosphates. These have the same structure as the orthophosphates of the ceric rare earths, but they also have a third crystalline phase of quadratic structure at high temperature (about 1,700° C.).

A third suitable family of orthophosphates of the rare earths includes the orthophosphates of the heavy rare earths, also designated yttric rare earths, and including Y, Ho, Er, Tm, Yb and Lu. Such compounds crystallize only in quadratic phase.

Of the various categories of rare earth orthophosphates indicated above, the orthophosphates of the light rare earths are the preferred.

It is also within the ambit of the invention to use any oxygenated compound of phosphorus, which, during the synthesis of the catalyst or during the subject reaction, forms an orthophosphate of a rare earth metal.

The orthophosphates or the initial rare earth metals which are used in the process of the invention are known compounds. Commercial such phosphates can thus be used, in particular lanthanum orthophosphate, or they can be synthesized according to known technique.

General techniques for the production of such phosphates are described, in particular, in PASCAL P., *Nouveau Traité de Chimie Minérale*, volume X, pp. 821–823 (1956) and *Gmelins Handbuch der anorganischen Chemie*, 8th edition, vol. 16 (C), pp. 202–206 (1965). Two principal processes are typical for preparing these phosphates: first, precipitating a soluble metal salt (chloride, nitrate) with ammonium hydrogenophosphate or with phosphoric acid; secondly, reacting the metal oxide with phosphoric acid under hot conditions. In both instances, a final treatment with an alkaline hydroxide is conventional.

The phosphates of said metals can also be prepared by firing (solid/solid reaction) their salts with phosphorus salts, and then calcining same.

Such preparative techniques are described, more particularly, in FUKUO et al, *Nippon Kagakkai Shi*(Revue de l'Association japonaise de Chimie, (4), pp. 622–626 (1975), for cerium orthophosphate, in J. M. COWLEY et al, *Journal of Catalysis*, 56, pp. 185–194 (1979), for lanthanum orthophosphate, and in L. S. ESHCHENKO et al, *Russian Journal of Inorganic Chemistry*, 30, (6), (1985), for yttrium orthophosphate.

The product is then dried via conventional techniques well known to this art. The drying is advantageously carried out at a temperature of from 50° C. to 200° C., for a period of time which preferably ranges from 2 to 8 hours, in a normal atmosphere or at reduced pressure (for example 10 mm of mercury=1,300 Pa) or by lyophilization.

The dried product can then be calcined at a temperature of from 200° C. to 1,000° C., preferably from 400° C. to 600° C., for a period of time which ranges from 1 to 15 hours, preferably from 3 to 6 hours.

The product can be used directly as a catalyst, the calcination being carried out at the reaction temperature and under the conditions of the subject reaction.

When an orthophosphate of a trivalent rare earth metal is used which is not doped, one preferred embodiment of the invention comprises calcining the catalyst at high temperature prior to use, for example at a temperature ranging from 500° C. to 1,000° C., preferably at a temperature of from 700° C. to 800° C., for a period of time of from 1 to 15 hours, preferably from 3 to 6 hours.

Indeed, it has now surprisingly been determined that when a catalyst is used which has been calcined at high temperature, it is possible to improve the conversion rate of the phenol and selectivity of the reaction.

Another preferred embodiment of the invention entails using an orthophosphate of a trivalent rare earth which has been doped with an alkali metal or an alkaline earth metal.

The catalysts employed in the process of the invention are also known compounds and are described in EP-A-0,440,555, as are processes for the preparation thereof.

One method for the preparation of these compounds comprises impregnation of a compound of formula $MPO_4$, with M being as defined above, with an impregnating solution Imp, also as defined above, in a volatile solvent, preferably water.

The product $MPO_4$ can be chemically modified by dry or humid impregnation.

Thus, one such technique entails dry impregnation of the metal orthophosphate $MPO_4$ using a solution of at least one alkali metal or alkaline earth metal salt. As aforesaid, the preferred counter-anions are hydrogenophosphate or phosphate, preferably cesium hydrogenophosphate.

The impregnation operation is carried out under dry conditions, i.e., the entire volume of the solution used is approximately equal to the total pore volume of the orthophosphate of the trivalent rare earth metal. The product obtained is then dried and calcined.

In particular, the dry impregnation operation entails adding to a mass $m_1$ of a powder of the product to be impregnated, a volume V of an aqueous solution of one or more salts of the cations or anions to be fixed to the surface of the solids. The volume V of the solution is selected such that $V/m_1$ is equal to the pore volume in water of the solids to be impregnated.

The concentration C of cations or anions in the impregnating solution is selected such that the $CVM_2/m_1$ ratio is equal to the percentage by weight selected of the impregnating species fixed to the surface of the product to be impregnated (with $M_2$=molar mass of the impregnating species). The solution is added dropwise in such manner as to provide homogeneous adsorption.

The product is then maintained at rest for a variable period of time at ambient temperature. It is then dried via conventional techniques known to this art. The drying operation is usually carried out at atmospheric pressure, or at reduced pressure, or by lyophilization. The product can also be calcined.

Humid or moist impregnation is carried out by dispersing the orthophosphate of a trivalent rare earth metal in an aqueous solution of salts of cations and/or anions to be fixed to the surface of the solids.

The concentration of the impregnating species in the solution advantageously ranges from $10^{-3}$M to 10M.

The pH of the solution can advantageously be adjusted to a value which is at least equal to that of the isoelectric point of the product to be modified, in order to preferably fix the cations (usual case); however, this condition is not critical. It is possible to properly fix the cations below this isoelectric point when the associated anions are very "covalent" in nature, as the sulfates or phosphates.

The temperature of the solution advantageously ranges from ambient temperature to 100° C.

The dispersion is agitated vigorously for a variable period of time.

The product is then filtered and optionally washed.

In the above two embodiments for preparation of said chemical compounds, the drying operation is advantageously carried out at a temperature which ranges from 50° C. to 200° C. for a period of time which preferably ranges from 2 to 8 hours.

Insofar as the calcination operation is concerned, it is advantageously carried out at a temperature ranging from 200° C. to 1,000° C., preferably from 400° C. to 700° C. for a period of time which ranges from 1 to 15 hours, preferably from 3 to 6 hours.

The preferred catalysts of the invention correspond to formula (III) in which M is lanthanum, cerium or samarium, optionally doped with an alkali metal, preferably cesium.

The catalysts according to the present invention are such that the face surface area of the catalytic shaped articles comprises, at least in part, a compound as described above.

The catalytic phase can be used pure (as such) or it can be deposited onto suitable support. In the description which follows, the term "catalytic body" connotes the special unitary shape of the catalyst, whether or not the catalyst comprises a support. The catalytic phase is deposited onto the support via any known technique.

The catalytic bodies can have any per se known shape for solid catalysts which can be used for gaseous phase reactions.

The residue of said catalytic body, namely, the portion of which that does not come into contact with the gaseous reaction mixture can be of any material(s), provided that it/they is/are inert under the conditions of use. For the sake of simplifying production, it can be composed of compounds selected from among the phosphates, hydrogenophosphates, and mixtures thereof. The catalysts can also be shaped entirely from chemical compounds (III) according to the present invention.

The catalyst can be in various forms: powder, or shaped articles such as granules (for example, cylinders), beads, pellets, or monoliths (honeycomb-shaped blocks) which are produced by extrusion, molding, compacting, or any other known process.

The specific surface area of the catalyst is as large as possible, usually being at least equal to 1 m², advantageously being at least equal to 10 m², typically ranging from 50 to 150 m²/g and preferably from 50 to 100 m²/g.

According to the process of the invention, the O-alkylation reaction is carried out in vapor phase, by contacting the phenolic compound of formula (I) with the catalyst.

The amount of alkanol used is equal to or greater than the stoichiometric amount required to etherify one or more hydroxyl groups into alkoxy (or aralkoxy) groups.

Usually, the amount of alkanol is such that the ratio between the number of hydroxyl functions borne by the alkanol and the number of hydroxyl functions of the phenolic compound of formula (I) ranges from 0.5 to 500, preferably from 1 to 5.

As regards the catalyst, its productivity by weight and per hour advantageously ranges from 0.1 to 20 $h^{-1}$, preferably from 1 to 5 $h^{-1}$. The productivity by weight per hour of a catalyst is defined by the weight ratio between the phenolic compound introduced per hour and the catalyst.

It is reiterated that it is preferable to calcine the catalyst at a high temperature, prior to use, when an undoped rare earth metal orthophosphate is used.

The vector gas is optional, and is usually a gas or a mixture of non-reacting gases under reaction conditions. It is possible to use gases such as nitrogen, air, argon or helium. Advantageously, the ratio per volume between the vector gas and the phenolic compound ranges from 0 to 10, preferably from 0.1 to 2.0.

The reaction temperature of the O-alkylation operation typically ranges from 150° C. to 500° C., preferably from 200° C. to 350° C.

The reaction pressure advantageously ranges from $10^{-2}$ to 50 bars, and preferably is atmospheric pressure.

According to the process of the invention, the initial reagents are vaporized, namely, the phenolic compound and the alkanol. They are contacted with the catalyst, preferably while entrained by a vector gas.

The contact time, which is defined as the ratio between the apparent volume of the catalyst and the flow rate of the gaseous flowstream (including the vector gas), can vary widely, and advantageously ranges from 0.5 to 100 seconds. The contact time preferably ranges from 1 to 10 seconds.

Another preferred embodiment of the process of the invention includes adding water which is also vaporized. It is desirable that such quantity not be too great. Thus, the molar ratio between the water and the phenolic compound advantageously ranges from 0 to 5, preferably from 0.1 to 1.

In one example of actual practice, the catalytic bed is prepared initially which is constituted by the active catalytic phase deposited onto a support (for example, fitted glass) which permits the gases to circulate without elution of the catalyst. The reagents are then used and several embodiments are possible.

It is possible to vaporize each of the reagents, phenolic compound, alkanol and optionally water, in different chambers, and to then mix them in a mixing chamber and to introduce the resulting gaseous flowstream onto the catalyst. The vector gas can be introduced in parallel to said gaseous flowstream, or in the mixing chamber.

Another embodiment entails preparing a solution comprising the phenolic compound, alkanol and optionally water, and then vaporizing this mixture and introducing it onto the catalyst, in parallel with the vector gas.

Another technique for carrying out the subject process entails melting the phenolic compound by heating it to its melting point and then passing thereover a gaseous flow comprising the alkanol and optionally water. The flow is saturated with phenolic compound and it is then contacted with the catalyst.

Another technique is to use an organic solvent which is selected such that it solubilizes the phenolic compound and the alkanol.

According to the invention, it is preferable to use a polar aprotic solvent having a boiling point above 80° C. to 300° C.

Exemplary such polar aprotic solvents which can be used in the process of the invention include cyclic carboxamides such as N-methylpyrrolidone, and aliphatic or aromatic nitriles such as acetonitrile, propionitrile or benzonitrile.

The preferred solvents are ethers, and, in particular, dimethyl ethers deriving from ethylene oxide or propylene oxide, such as ethylene glycol dimethylether (or 1,2-dimethoxyethane), diethyleneglycol dimethylether (or 1,5-dimethoxy-3-oxapentane), 1,8-dimethoxy-3,6-dioxaoctane, 1,11-dimethoxy-3,6,9-trioxaundecane, 1,2-dimethoxy-1-methylethane, 1,5-dimethoxy-1,4-dimethyl-3-oxapentane, 1,7-dimethoxy-1,4-dimethyl-3,6-dioxaoctane.

More than one solvent can also be used.

Among the above solvents, ethyleneglycol dimethylether and diethyleneglycol dimethylether are the preferred.

The amount of phenolic compound in the solvent is typically such that the molar ratio of solvent/phenolic compound ranges from 0 to 20 and preferably from 0 to 5.

Thus, an organic solution is prepared which comprises the phenolic compound, alkanol and optionally water, and then said mixture is vaporized and is introduced over the catalyst, in parallel with the vector gas.

At the end of the reaction, all of the gases are condensed and the unreacted reagents and the products obtained are separated by distillation. It is also possible to separate them by fractional condensation.

Alkoxylated aromatic compounds are thus prepared which correspond to formula (IV).

wherein A is the residue of a monocyclic or polycyclic, aromatic carbocyclic radical, or a divalent radical comprising a chain or backbone of two or more monocyclic aromatic carbocyclic radicals; R is one or more "inert" substituents, which may be the same or different; R' is a hydrocarbon radical having 1 to 24 carbon atoms, selected from a linear or branched, saturated or unsaturated acyclic aliphatic radical, a monocyclic or polycyclic, aromatic, saturated or unsaturated, cycloaliphatic radical, or a linear or branched, saturated or unsaturated aliphatic radical substituted by a cyclic substituent; and n is a number which is less than or equal to 5.

The residue A can also be substituted by other hydroxyl groups; polyalkoxylated compounds can thus be prepared.

The process of the invention is well suited for the preparation of mono- or polyalkoxylated aromatic compounds via condensation of the following phenolic compounds corresponding to formula (I):

Phenol,
Hydroquinone,
Pyrocatechin,
2-Methoxyphenol,
3-Methoxyphenol,
4-Methoxyphenol,
2-Ethoxyphenol,
3-Ethoxyphenol,
4-Ethoxyphenol,
Salicyclic aldehyde,
p-Hydroxybenzaldehyde,
Methyl salicylate,
Methyl ester of p-hydroxybenzoic acid,
2-Chlorophenol,
4-Chlorophenol,
2-Nitrophenol,
4-Nitrophenol,
N-Acetyl-para-aminophenol,
Vanillin,
Isovanillin,
2-Hydroxy-5-acetamidobenzaldehyde
2-Hydroxy-5-propionamidobenzaldehyde,
4-Allyloxybenzaldehyde,
2,4-Dichlorophenol,
2,6-Dichlorophenol,
Methylhydroquinone,
Pyrogallol,
4-Bromovanillin,
4-Hydroxyvanillin,
2,4,6-Trichlorophenol,
3,5-Dimethoxy-4-hydroxybenzaldehyde,
6-Bromo-2-naphthol, with the following alkanols:
Methanol,
Ethanol,
Isopropanol,
Ethylene glycol,
Glycerol,
Cyclohexanol,
Benzyl alcohol.

The process of the present invention is particularly well suited for the preparation of anisole, guaiacol, guaethol, p-methoxyphenol and ethylene dioxybenzene. The preferred catalysts are lanthanum, cerium or samarium orthophosphate, optionally doped with cesium.

One advantage of this invention is that ethers of phenolic compounds are obtained with a good degree of conversion of the initial phenol and with good reaction selectivity.

Another advantage of the process of the invention is that the catalyst employed has remarkable stability. It therefore has a very long life because it does not become deactivated.

In the event of O-methylation of pyrocatechin, the process of the invention is particularly desirable because the production of the guaiacol or veratrole can be modulated, in accordance with market requirements. Thus, the O-methylation of hydroquinone permits p-methoxyphenol and/or p-dimethoxybenzene to be obtained.

In order to further illustrate the present invention and the advantages thereof, the following specific examples are given, it being understood that same are intended only as illustrative and in nowise limitative.

EXAMPLES

In the various examples to follow, the abbreviations TT, RR, RT have the following definitions:

Degree of Conversion: $TT = \dfrac{\text{number of moles of phenol converted in \%}}{\text{number of moles of phenol introduced}}$ Actual Yield: $RR = \dfrac{\text{number of moles of alkyl aryl ether formed in \%}}{\text{number of moles of phenol introduced}}$ Selectivity: $RT = \dfrac{\text{number of moles of alkyl aryl ether formed in \%}}{\text{number of moles of phenol transformed}}$

EXAMPLE 1

106 g of $H_3PO_4$ (85% concentration, marketed by Prolabo), namely, 0.92 mole in 800 ml of deionized water, were introduced into a reactor.

The contents of the reactor were agitated at 500–700 revs/minute.

299 g La$_2$(CO$_3$)$_3$·12 H$_2$O were introduced under cold conditions (i.e., 0.8 mole of lanthanum in 736 ml water) slowly and with vigorous agitation.

The reaction medium was then heated to 80° C., for two and one-half hours.

It was permitted to cool until ambient temperature was attained, without agitation, for one-half hour, and the operation was completed in a bath of cold water.

The suspension was filtered over a No. 3 fritted glass filter until the mother liquors were depleted.

The product was then dispersed again in 2 liters of water with vigorous agitation and was permitted to remain in suspension for one-half hour, while maintaining agitation conditions.

The suspension was filtered on a No. 3 fritted glass filter until the mother liquors were depleted.

The product was dispersed again in 900 ml deionized water and was neutralized with an aqueous solution of ammonia until a pH of 9 was reached.

The product was filtered, washed in water, centrifuged, and dried at 110° C.

EXAMPLE 2

To 4.7 ml of an aqueous 6M solution of CsOH, 14.12 ml of a 1M aqueous solution of H$_3$PO$_4$ were added. Water was then added to provide a final volume of 50 ml.

50 g of the product prepared in Example 1 were placed into a 200 ml beaker.

20 ml of the above impregnation solution were introduced dropwise, crushing the agglomerates formed and the mixture was homogenized.

The product was maintained at rest for one hour. It was dried overnight at 110° C. and was then calcined for 2 hours at 500° C.

Dry solids content of cesium=3%.

EXAMPLE 3

3 ml lanthanum phosphate catalyst prepared in accordance with the procedure of Example 2 (i.e., 3.0 g) were charged onto fritted glass, in a tubular quartz reactor having an internal diameter of 10 mm. The catalyst was surmounted by a bed of glass beads which were intended to render the gaseous flowstream homogeneous, prior to contact with the catalyst. Nitrogen was introduced in parallel at the top of the reactor using a Brooks flowmeter, and a solution of phenol was introduced into methanol using a pressure syringe.

At the outlet of the reactor, the gaseous effluents were condensed into two traps, in series, the first having been cooled by a bath of icewater and the second having been cooled by a bath of acetone/dry ice. The trapped substances were combined, diluted and then analyzed by high performance liquid chromatography (HPLC).

The reaction was carried out using a nitrogen flow rate of 1.2 l/h and a feed rate of solution of 6.4 ml (liquid) per hour. The molar ratio of methanol/phenol was 10.

After 1 hour of reaction at 300° C., the following results were obtained:

TT$_{phenol}$=10.6%
RR$_{anisole}$=10.0%
RT$_{anisole}$=94.3%

The reaction was also carried out for 1 hour at 330° C. and at 360° C., with the following results:

TABLE I

| Temperature (°C.) | Phenol TT(%) | Anisole RR(%) | Anisole RT(%) |
|---|---|---|---|
| 330 | 22.7 | 21.7 | 90.87 |
| 360 | 52.7 | 48.6 | 89.0 |

EXAMPLE 4

The procedure of Example 3 was repeated, except that 2.5 ml of catalyst LaPO$_4$ were used, prepared according to Example 1 and corresponding to 2.0 g.

A solution of pyrocatechin in methanol (molar ratio of methanol/pyrocatechin=10) was injected at a flow rate of 5 ml/h.

After 1 hour of reaction at 270° C., the following results were obtained:

TT$_{pyrocatechin}$=60%
RR$_{guaiacol}$=59%
RT$_{guaiacol}$=98.3%

The same conditions were employed at a temperature of 330° C., and the following results were then obtained:

TT$_{pyrocatechin}$=88.1%
RR$_{guaiacol}$=56.6%
RT$_{guaiacol}$=64.2%
veratrole: trace amounts

EXAMPLE 5

The procedure of Example 2 was repeated, using an impregnation solution which had been prepared from 11 ml of a 6M aqueous solution of CsOH and 33 ml of a 1M aqueous solution of H$_3$PO$_4$.

The dry solids content of cesium was 7%.

EXAMPLE 6

The procedure of Example 2 was repeated, using an impregnation solution which had been prepared from 15.67 ml of a 6M aqueous solution of CsOH and 23.5 ml of a 2M aqueous solution of H$_3$PO$_4$.

The dry solids content of cesium was 10%.

EXAMPLE 7

A reaction was carried out under identical conditions as those of Example 4, using 2.5 ml of the catalyst prepared in Example 6.

After 1 hour of reaction at 270° C., the following results were obtained:

TT$_{pyrocatechin}$=40.5%
RR$_{guaiacol}$=40%

The same conditions were used to carry out the reaction at 300° C., 330° C. and 360° C. The results after one hour at each of these temperatures are reported in the following Table:

TABLE II

| Temperature | Pyrocatechin | Guaiacol | | Veratrole | |
|---|---|---|---|---|---|
| (°C.) | TT % | RR(%) | RT(%) | RR(%) | RT(%) |
| 300 | 52.2 | 51.0 | 97.8 | Traces | — |
| 330 | 85.7 | 71.0 | 82.3 | 8.0 | 9.7 |
| 360 | 97.0 | 62.6 | 64.5 | 25.1 | 25.9 |

EXAMPLE 8

The reaction was carried out under the same conditions as those of Example 4, using 2.5 ml of the catalyst prepared in Example 5.

After 1 hour of reaction at 270° C., the following results were obtained:

$TT_{pyrocatechin}=26.6\%$ $RR_{guaiacol}=26.6\%$

The same conditions were employed in carrying out the reaction at 300° C., 330° C. and 360° C. The results after one hour at each of these temperatures are reported in the following Table:

TABLE III

| Temperature | Pyrocatechin | Guaiacol | | Veratrole | |
|---|---|---|---|---|---|
| (°C.) | TT % | RR(%) | RT(%) | RR(%) | RT(%) |
| 300 | 61.2 | 58.4 | 95.5 | 2.6 | 4.2 |
| 330 | 86.7 | 69.6 | 80.3 | 17.0 | 19.5 |
| 360 | 94.2 | 67.2 | 71.4 | 26.8 | 28.5 |

EXAMPLE 9

The synthesis described in Example 1 was reproduced, substituting $Ce_2(CO_3)_3$ for $La_2(CO_3)_3$ (mole per mole).

EXAMPLE 10

91.2 g $H_3PO_4$ (85% concentration, marketed by Prolabo) and 340 ml water were introduced into a 2 liter reactor.

The contents of the reactor were at 500–700 revs/minute. The medium was heated to 90° C.

140.93 g $Sm_2O_3$ were added (prepared via the calcination, at 700° C., of $Sm_2(CO_3)_3$ marketed by Rhone-Poulenc) in portions over a period of 30–40 minutes with agitation (2 to 3 spatulas at a time, all for 4 to 5 minutes).

The temperature of the reaction mixture was maintained from 87° to 93° C., for 3 hours.

The product was then filtered, washed on fritted glass 3 times and dried at 110° C. overnight.

EXAMPLE 11

10 g of the product prepared in Example 10 were impregnated with 11.7 ml of the 50 ml solution of CsOH and $H_3PO_4$ prepared from 5.16 ml CsOH 3M and 7.74 ml $H_3PO_4$ 1M, in accordance with the procedure of Example 2.

EXAMPLES 12 AND 13

A reaction was carried out under the same conditions as in Example 4. 2.5 ml $CePO_4$ (Example 12) and $SmPO_4$ (Example 13) were used.

The preparation of the $CePO_4$ was as in Example 9, and the $SmPO_4$ was prepared according to the technique described in Example 10.

The results obtained after 1 hour of operation at 270° C. and 360° C. are reported in the following Table:

TABLE IV

| | Temperature 270° C. | | | Temperature 360° C. | | |
|---|---|---|---|---|---|---|
| Catalyst | TT(%) PC | RT(%) Guaiacol | RT(%) Veratrole | TT(%) PC | RT(%) Guaiacol | Veratrole |
| $CePO_4$ | 60.5 | 92.0 | 4.6 | 95.4 | 2.4 | 6.2 |
| $SmPO_4$ | 87 | 93 | 6.5 | 97.5 | 12 | 4.7 |

EXAMPLE 14

A reaction was carried out under the identical conditions of Example 4, using 2.5 ml of the catalyst prepared in Example 11.

The results after 1 hour of operation at various temperatures are reported in the following Table:

TABLE V

| Temperature | Pyrocatechin | Guaiacol | | Veratrole | |
|---|---|---|---|---|---|
| (°C.) | TT(%) | RR(%) | RT(%) | RR(%) | RT(%) |
| 270 | 14.1 | 14.1 | 100 | — | — |
| 300 | 33.0 | 32.9 | 99.7 | — | — |
| 330 | 64.6 | 64.5 | 99.8 | — | — |
| 360 | 91.2 | 87.1 | 95.5 | 3.9 | 4.3 |
| 390 | 97.5 | 86.8 | 89 | 10.5 | 10.8 |

EXAMPLE 15

The catalyst of Example 6 was employed under the following conditions:

(a) Temperature: 300° C.

(b) Flow rate of nitrogen: 0.5 l/h (c) Flow rate of the solution of pyrocatechin in methanol: 5/ml/h (d) Methanol/pyrocatechin molar ratio: 10

The following results were obtained at various stages of the reaction:

TABLE VI

| 2 hours | TT = 42.3% | $RR_{guaiacol}$ = 42.5% |
|---|---|---|
| 3 hours | TT = 42.8% | $RR_{guaiacol}$ = 42.8% |
| 4 hours | TT = 44.7% | $RR_{guaiacol}$ = 42.0% |
| 6 hours | TT = 42.6% | $RR_{guaiacol}$ = 42.5% |

EXAMPLE 16

A solution of pyrocatechin in ethylene glycol was reacted, using the same catalyst as that described in Example 6. The following conditions were employed:

(a)$_{2.5}$ ml catalyst (2.6g)

(b) Nitrogen flow rate: 1.2 l/h (e) Flow rate of the pyrocatechin solution in ethylene glycol: 2.9 ml/h (d) Ethylene glycol/pyrocatechin molar ratio: 10

After 1 hour of reaction at 330° C., the following results were obtained:

TT=100%

The only compound determined by chromatography in gaseous phase (GPC) and by HPLC was ethylene dioxybenzene.

At 270° C. and 300° C., an intermediate compound was detected whose structure, as determined by mass spectrography was:

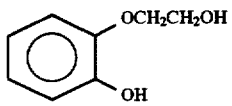

EXAMPLE 17

A solution of hydroquinone, methanol and water (hydroquinone/water/methanol molar ratio=1/7/16) was injected into the reactor at 330° C. at a flow rate of 2.8 ml/h onto a catalyst bed (2.5 ml corresponding to 2.57 g) prepared in accordance with Example 6. The nitrogen flow rate was 1.2 l/h.

After one hour of reaction, the following results were obtained:

TT=25.8%

$RR_{p\text{-}methoxyphenol}$=24.2%

$RT_{p\text{-}methoxyphenol}$=94.1%

The principal byproduct was methylhydroquinone. Only trace amounts of p-dimethoxybenzene were detected.

EXAMPLE 18

106 g of $H_3PO_4$ were introduced into a reactor (85% concentration, marketed by Prolabo), i.e., 0.92 mole in 800 ml of deionized water.

The contents of the reactor were agitated at 500–700 revs/minute.

299 g of $La_2(CO_3)_3 \cdot 12\ H_2O$ were introduced under cold conditions (namely, 0.8 mole of lanthanum in 800 ml water), slowly and with vigorous agitation.

The reaction medium was then heated to 80° C., for two and one-half hours.

It was permitted to cool to ambient temperature without agitation for one-half hour, and the operation was concluded in a bath of cold water.

The suspension was filtered on a No. 3 fritted glass filter until the mother liquors were exhausted.

The product was then dispersed again in 2 liters of water, with vigorous agitation, and was maintained in suspension for one-half hour, with agitation being maintained.

This washing operation was carried out twice following the same procedure.

The product thus washed was dried at 110° C.

EXAMPLE 19

The product prepared according to the procedure of Example 18 was calcined for 3 hours at 700° C.

EXAMPLE 20

182.4 g of $H_3PO_4$ (85% concentration, marketed by Prolabo), i.e., 1.6 mole in 640 ml deionized water, were introduced into a reactor.

The reaction medium was heated to 85° C., and 260.8 g of $La_2O_3$ were introduced (namely, 0.8 mole of lanthanum) uniformly (14 g every 5 minutes).

The reaction mixture was heated for 1 hour at 85° C., and it was then permitted to cool to ambient temperature, with agitation.

The product was recovered by centrifugation (3,600 revs/min), and it was then dispersed again in 400 ml deionized water.

The product thus washed was recovered by centrifugation.

This washing operation was carried out 3 times following the same procedure.

The product thus washed was dried at 110° C.

EXAMPLE 21

The product prepared according to the procedure of Example 20 was calcined for 3 hours at 700° C.

EXAMPLE 22

A reaction was carried out under conditions identical to those of Example 3.

The catalyst of Example 18 was employed under the following conditions:

Catalyst: 3.5 g

Calcination: 2 hours at 400° C., with nitrogen (2.2 l/h)

Reaction:

Temperature: 330° C.

Nitrogen flow rate: 2.2 l/h

A solution of pyrocatechin in 3 equivalents of ethanol was introduced at a flow rate of 6.2 g/h.

After 1 hour of reaction, the following results were obtained:

$TT_{pyrocatechin}$=31%

$RT_{guaethol}$=56%

EXAMPLE 23

The catalyst of Example 19 was employed under the conditions of Example 22.

After 1 hour of reaction, the following results were obtained:

$TT_{pyrocatechin}$=33%

$RT_{guaethol}$=90%

EXAMPLE 24

The catalyst of Example 20 was employed under the conditions of Example 22.

After 1 hour of reaction, the following results were obtained:

$TT_{pyrocatechol}$=54%

$RT_{guaethol}$=55%

EXAMPLE 25

The catalyst of Example 21 was employed under the conditions of Example 22.

After 1 hour of reaction, the following results were obtained:

$TT_{pyrocatechol}$=40%

$RT_{guaethol}$=80%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a carbocyclic/aliphatic ether, comprising reacting a phenolic compound with an alcohol, in gaseous phase, in the presence of a catalytically effective amount of a trivalent rare earth metal orthophosphate, wherein the trivalent rare earth metal orthophosphate is a compound in which the molar ratio between the phosphate anion and the trivalent rare earth metal cation is about 1 plus or minus 0.2.

2. The process as defined by claim 1, said phenolic compound having the general formula (I):

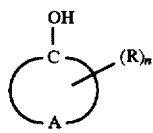     (I)

wherein A is the divalent variable of a monocyclic or polycyclic, aromatic carbocyclic group, or a divalent group comprising a structural unit of two or more monocyclic aromatic carbocyclic groups; R is one or more inert substituents, which may be the same or different; and n is a number less than or equal to 5.

3. The process as defined by claim 2, said alcohol having the general formula (II):

R'—OH     (II)

wherein R' is a hydrocarbon group having from 1 to 24 carbon atoms selected from among a linear or branched, saturated or unsaturated acyclic aliphatic group; a monocyclic or polycyclic, saturated or unsaturated cycloaliphatic group; or a linear or branched, saturated or unsaturated aliphatic group bearing a cyclic substituent.

4. The process as defined by claim 2, wherein formula (I), the groups R, which may be the same or different, are each a hydrogen atom; a linear or branched alkyl group having from 1 to 6 carbon atoms; a linear or branched alkenyl group having from 2 to 6 carbon atoms; a linear or branched alkoxy group having from 1 to 6 carbon atoms; an acyl group having from 2 to 6 carbon atoms; or a group having one of the formulae:

—R$_1$—OH
—R$_1$—COOR$_2$
—R$_1$—CHO
—R$_1$—NO$_2$
—R$_1$—CN
—R$_1$—(NR$_2$)$_2$
—R$_1$—CO—(NR$_2$)$_2$
—R$_1$—X
—R$_1$—CF$_3$ in which R$_1$ is a simple valence bond or a saturated or unsaturated, linear or branched, divalent hydrocarbon group having from 1 to 6 carbon atoms; R$_2$ is a hydrogen atom or a linear or branched alkyl group having from 1 to 6 carbon atoms; and X is a halogen atom.

5. The process as defined by claim 4, wherein formula (I), the groups R, which may be same or different, are each a hydrogen atom, an —OH group, a linear or branched alkyl group having from 1 to 6 carbon atoms, a linear or branched alkenyl group having from 2 to 6 carbon atoms, a linear or branched alkoxy group having from 1 to 6 carbon atoms, a —COOR$_2$ group, a —NO$_2$ group, a halogen atom, or a —CF$_3$ group, and n is 0, 1, 2 or 3.

6. The process as defined by claim 2, wherein formula (I) the variable A is a monocyclic or polycyclic aromatic carbocyclic group, the ring members of which together form an orthocondensed structural unit having the formula (Ia):

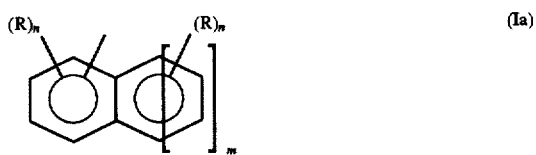     (Ia)

in which m is 0, 1 or 2.

7. The process as defined by claim 2, wherein formula (I) the variable A is a group comprising at least two monocyclic aromatic carbocyclic groups and having the formula (Ib):

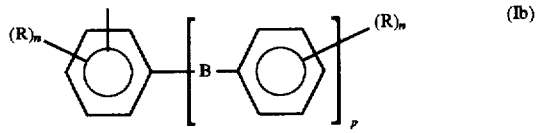     (Ib)

in which p is a number equal to 0, 1, 2 or 3 and B is a simple valence bond, an alkylene or alkylidene group having from 1 to 4 carbon atoms, or one of the groups of the formulae:

—O—, —CO—, —COO—, —OCOO—,
—S—, —SO—, —SO$_2$—,

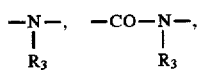

wherein R$_3$ is a hydrogen atom, an alkyl group having from 1 to 4 carbon atoms, or a cyclohexyl or phenyl group.

8. The process as defined by claim 6, wherein formula (Ia), R is a hydrogen atom, a hydroxyl group, a —CHO group, an —NO$_2$ group, a linear or branched alkyl or alkoxy group having from 1 to 6 carbon atoms; m is equal to 0 or 1; and n is equal to 0, 1 or 2.

9. The process as defined by claim 7, wherein formula (Ib), R is a hydrogen atom, a hydroxyl group, a —CHO group, an —NO$_2$ group, a linear or branched alkyl or alkoxy group having from 1 to 6 carbon atoms; B is a simple valence bond, an alkylidene or alkylene group having from 1 to 4 carbon atoms, or an oxygen atom; n is equal to 0, 1 or 2; and p is equal to 0 or 1.

10. The process as defined by claim 2, said phenolic compound of formula (I) being phenol, hydroquinone, pyrocatechin, 2-methoxyphenol, 3-methoxyphenol, 4-methoxyphenol, 2-ethoxyphenol, 3-ethoxyphenol, 4-ethoxyphenol, salicylic aldehyde, p-hydroxybenzaldehyde, methyl salicylate, methyl ester of p-hydroxybenzoic acid, 2-chlorophenol, 4-chlorophenol, 2-nitrophenol, 4-nitrophenol, N-acetyl-para-aminophenol, vanillin, isovanillin, 2-hydroxy-5-acetamidobenzaldehyde, 2-hydroxy-5-propionamidobenzaldehyde, 4-allyloxybenzaldehyde, 2,4-dichlorophenol, 2,6-dichlorophenol, methylhydroquinone, pyrogallol, 4-bromovanillin, 4-hydroxyvanillin, 2,4,6-trichlorophenol, 3,5-dimethoxy-4-hydroxybenzaldehyde, or 6-bromo-2-naphthol.

11. The process as defined by claim 3, wherein formula (II), the group R' is a linear or branched alkyl, alkenyl, alkadienyl or alkynyl group having from 1 to 24 carbon atoms, the hydrocarbon backbone of which optionally being interrupted by one of the groups:

—O—, —CO—, —COO—, —OCOO—, —S—, —SO$_2$—,

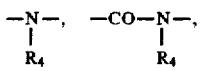

wherein $R_4$ is a hydrogen atom, or a linear or branched alkyl group having from 1 to 4 carbon atoms, and/or is substituted by one of the following substituents:

—OH, —OCOO—, —COOR$_4$, —CHO, —NO$_2$, —X—, —CF$_3$.

12. The process as defined by claim 11, wherein formula (II), the group R' is substituted by a cyclic substituent, bonded thereto via a valence bond or one of the groups:

—O—, —CO—, —COO—, —OCOO—, —S—, —SO$_2$—,

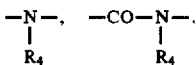

13. The process as defined by claim 3, said alcohol having the formula (II) comprising methanol, ethanol, isopropanol or ethylene glycol.

14. The process as defined by claim 1, said trivalent rare earth metal orthophosphate having the formula (III):

$$MPO_4(lm)_p \quad (III)$$

wherein M is an $M_3$ trivalent rare earth, or a mixture of at least one $M_3$ trivalent rare earth and at least one $M_1$ alkali metal or $M_2$ alkaline earth metal according to the equation:

$$M=\alpha M_1^+ + \beta M_2^{++} + \gamma M_3^{3+} \text{ and } \alpha+2\beta+3\gamma=3;$$

lm is a basic impregnation compound comprising an alkali metal or alkaline earth metal associated with a counter-anion to provide electrical neutrality; α is a coefficient ranging from 0 to 3; β is a coefficient ranging from 0 to ½; γ is a coefficient ranging from 0 to 1; and p is a number less than 0.5.

15. The process as defined by claim 14, wherein formula (III), $M_1$ is at least one element of Group 1A of the Periodic Table; $M_2$ is at least one element of Group 2A of the Periodic Table; and $M_3$ is at least one trivalent rare earth.

16. The process as defined by claim 15, wherein formula (III), $M_1$ is lithium, sodium, potassium, rubidium, cesium, or mixture thereof; $M_2$ is beryllium, magnesium, calcium, strontium, barium, or mixture thereof; and $M_3$ is yttrium, scandium, lanthanum, cerium, praseodymium, neodymium, samarium, europium, gadolinium, terbium, dysprosium, holmium, erbium, thulium, ytterbium, lutecium, or mixture thereof.

17. The process as defined by claim 14 said orthophosphate of formula (III) comprising a ceric rare earth and being doped with an alkali and/or alkaline earth metal.

18. The process as defined by claim 16, said orthophosphate of formula (III) comprising lanthanum, cerium or samarium and being doped with an alkali metal.

19. The process as defined by claim 14, said orthophosphate of formula (III) comprising up to 25% by weight of a dopant.

20. The process as defined by claim 19, said orthophosphate of formula (III) comprising from 3% to 15% by weight of a dopant.

21. The process as defined by claim 14, wherein said orthophosphate of formula (III), α and β are 0 and said orthophosphate being calcined.

22. The process as defined by claim 21, said orthophosphate of formula (III) having been calcined at a temperature ranging from 500° C. to 1,000° C. for from 1 to 15 hours.

23. The process as defined by claim 18, said orthophosphate of formula (III) being doped with cesium.

24. The process as defined by claim 1, wherein the ratio between the number of hydroxyl functions borne by said alcohol to the number of hydroxyl functions of said phenolic compound ranges from 0.5 to 500.

25. The process as defined by claim 24, said ratio ranging from 1 to 5.

26. The process as defined by claim 1, carried out at a temperature ranging from 150° to 500° C.

27. The process as defined by claim 1, carried out in the presence of water.

28. The process as defined by claim 1, said phenolic compound and said alcohol being solubilized in an organic solvent.

29. The process as defined by claim 1, comprising reacting pyrocatechin with methanol and/or ethanol.

30. The process as defined by claim 1, comprising reacting phenol with methanol.

31. The process as defined by claim 1, comprising reacting hydroquinone with methanol.

32. The process as defined by claim 1, comprising reacting pyrocatechin with ethylene glycol.

33. The method of claim 1 wherein the ratio is 1.

* * * * *